United States Patent [19]

Willert et al.

[11] Patent Number: 4,919,673

[45] Date of Patent: Apr. 24, 1990

[54] PROSTHESIS FOR A FEMORAL HEAD

[75] Inventors: Hans-Georg Willert, Gottingen, Fed. Rep. of Germany; Manfred Semlitsch, Winterthur, Switzerland

[73] Assignee: Sulzer Brothers Limited, Winterthur, Switzerland

[21] Appl. No.: 315,731

[22] Filed: Feb. 24, 1989

[30] Foreign Application Priority Data

Feb. 29, 1988 [CH] Switzerland .................. 00746/88

[51] Int. Cl.$^5$ .............................................. A61F 2/36
[52] U.S. Cl. .................................... 623/23; 623/16
[58] Field of Search ............... 623/23, 22, 16, 18–20; 128/92 YZ, 92 YK, 92 VP, 92 VD

[56] References Cited

U.S. PATENT DOCUMENTS

| 3,896,505 | 7/1975 | Timmermans | 623/23 |
| 4,080,666 | 3/1978 | Fixel | 623/23 X |
| 4,561,432 | 12/1985 | Mazor | 128/92 YK |
| 4,705,032 | 11/1987 | Keller | 623/23 X |

FOREIGN PATENT DOCUMENTS

| 0058744 | 9/1982 | European Pat. Off. | 623/16 A |
| 0143847 | 6/1985 | European Pat. Off. | 623/16 A |
| 3304476 | 9/1983 | Fed. Rep. of Germany | 623/22 |
| WO86/02260 | 4/1986 | World Int. Prop. O. | 623/22 |

Primary Examiner—Ronald L. Frinks
Attorney, Agent, or Firm—Kenyon & Kenyon

[57] ABSTRACT

The femoral head prosthesis has a straight fixing stem for implantation in a femur which is provided with a longitudinal bore which extends along the axis of the stem. The stem can be slid along a centering rod previously positioned within a surgically prepared bone cavity of the femur to guide the stem into a bone cement bed. The centering rod is initially put in place with a cavity barrier followed by placement of the bone cement bed. After initial curing of the bone cement, the rod can be disengaged from the cavity barrier and removed from the stem.

4 Claims, 1 Drawing Sheet

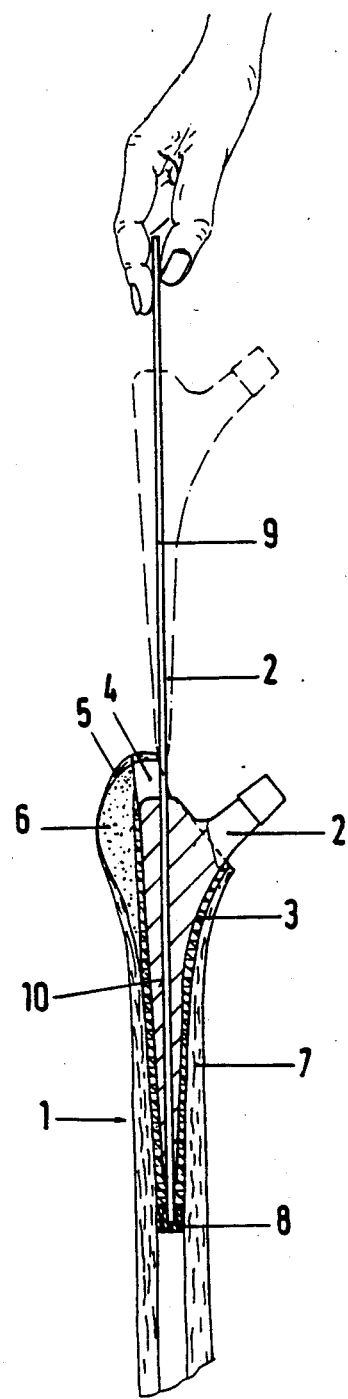

PROSTHESIS FOR A FEMORAL HEAD

This invention relates to a prosthesis for a femoral head. More particularly, this invention relates to a prosthesis having a straight fixing stem.

As is known, various types of stems have been provided for the implantation of a prosthesis in a bone. For example, various types of straight fixing stems have been used for the implantation of a prosthesis for a femoral head in a femur wherein the stem is fixed in place by means of a bone cement bed. For example, European Patent Application 0212084 describes a straight fixing stem which can be fixed in a cement bed.

In order to obtain a satisfactory adhesion of a prosthesis stem in a cement bed and of the bed in the surrounding bone tissue, the stem-enveloping bone cement must have a minimum thickness of, for example of 1 to 3 millimeters and must also be distributed very uniformly at least around the periphery of the stem. However, in the case of conventional prosthetic stems, this requirement has been difficult for the operating surgeon to satisfy since the surgeon has no possibility of centering and guiding the stem during introduction into an operation cavity containing a bone cement bed nor of retaining the stem in a centered position until the cement has cured sufficiently for the stem to be stabilized in position.

Accordingly, it is an object of the invention to facilitate the task of the operating surgeon in ensuring a centered fixing of a stem of a prosthesis in a cement bed.

It is another object of the invention to be able to implant a prosthesis stem in a bone cement bed within a femur bone while maintaining a uniform minimum thickness of cement between the stem and the bone cavity.

Briefly, the invention provides a prosthesis for a femoral head having a straight fixing stem for implanting in a femur wherein the stem has a bore extending along a longitudinal axis over the length of the stem which is of a size for receiving a centering rod for guiding the stem.

The centering rod which is sized for disposition in a bone cavity of a femur may also be secured, as by threading, to a bone marrow cavity barrier at a distal end of the rod.

At the time of implantation, the centering rod is used to position the bone marrow cavity barrier in place. Thereafter, the rod is used as a guide for the stem of the prosthesis. In this case, the rod is disposed and retained on the hypothetical central axis of the bone cavity before the bone cement is introduced into the cavity. Once the bone cement has been introduced into the cavity, the barrier, in known manner, seals the cement bed off from the interior of the bone. With the rod disposed and retained on the hypothetical central axis of the cavity, the stem is threaded onto the centering rod outside the bone, particularly if the length of the rod is at least twice the length of the stem. The stem is then guided and pressed into the soft bone cement and centered, particularly in the anterior/posterior and medial/lateral directions. Continued pressing of the prosthesis forces the stem along the centering rod into position within the femur bone cavity.

After implantation and positioning of the prosthesis stem, the centering rod is clamped or maintained as immobile as possible until the bone cement has cured sufficiently for the stem position to be stable. The centering rod can then be removed, for example, by unthreading from the cavity barrier and sliding outwardly from the prosthesis stem.

These and other objects and advantages of the invention will become more apparent from the following detailed description taken in conjunction with the accompanying drawing wherein:

The FIGURE illustrates a longitudinal view through a femur and a prosthesis at a point of implantation of the prosthesis in accordance with the invention.

Referring to the drawing, the femur 1 which has been opened by a cut made substantially perpendicularly to the femur neck is operatively formed with a cavity 4. Except in the vicinity of the greater trochanter 5, the cavity 4 is cleared of spongy tissue 6 as far as the edge of the cortex 7 and the tissue replaced by a bed of bone cement 3.

As indicated, the prosthesis for a femoral head (not shown) has a straight fixing stem 2 for implanting in the femur 1. As illustrated, the stem 2 has a bore 10 which extends along a longitudinal axis of the stem over the entire length from the distal end through the upper proximal end, as viewed. This bore 10 is sized so as to slidably receive a centering rod 9.

The centering rod 9 is of circular cross-section shape which is of a length at least twice the length of the stem 1. To this end, the length of the rod is such that the stem 2 can be completely slid onto the rod 9 outside the bone cavity 4, as shown in chain-dotted lines, before being pressed into the bone cement 3.

A bone marrow cavity barrier 8 of generally known construction is also releasably secured to the lower end of the rod 9, for example, by being threaded onto the rod 9.

During use, the rod 9 and cavity barrier 8 are fitted into the surgically prepared cavity 4 of the femur 1. Thereafter, a bed of bone cement 3 is formed within the cavity 4 in any suitable known manner with deeper penetration of the cement into the femur 1 being prevented by the barrier 8. Thereafter, with the rod 9 held on the central axis of the bone cavity 4, as from above, the prosthesis stem 2 is threaded onto the rod 9 into the chain-dotted position shown. Next, with rod 9 retained on the axis of the bone cavity 4, the stem 2 is pressed into the bed of bone cement 3. During this time, the stem 2 is guided into the bone cavity 4 such that a substantially uniform thickness of bone cement is obtained between the stem 2 an the interior wall of the femur 1.

As indicated, during pressing in of the stem 2, the rod is held at the upper end to facilitate guidance of the stem 2 into proper position.

After implantation of the stem 2, the rod 9 remains in place until the bone cement 3 has cured sufficiently to hold the stem 2 in place. Thereafter, the rod 9 is disengaged from the cavity barrier 8 and removed by being slid out of the stem 2.

The invention thus provides a relatively simple technique for guiding the straight stem of a prosthesis for a femoral head into position within a bone cement bed in a femur. Further, the invention facilitates the formation of a substantially uniform thickness of bone cement circumferentially about the straight stem of a femoral prosthesis during implantation.

What is claimed is:

1. In combination
   a centering rod for disposition in a bone cavity of a femur;
   a bond marrow cavity barrier detachably secured to a distal end of said rod; and a prosthesis for a femoral head having a longitudinally extending stem having a bore extending along a longitudinal axis of said stem, said bore having a diameter for slidably receiving said rod therein to guide said stem into the bone cavity.

2. The combination as set forth in claim 1 wherein said rod is at least twice the length of said stem.

3. In combination
a prosthesis for a femoral head having a longitudinally extending stem having a bore extending along a longitudinal axis of said stem;
a centering rod for disposition in a bone cavity of a femur, said rod having a length at least twice the length of said stem and of a diameter for sliding within said bore of said stem to guide said stem into the bone cavity; and
a bone marrow cavity barrier threadably secured to a distal end of said rod.

4. In combination
a centering rod for disposition in a bone cavity of a femur;
a bone marrow cavity barrier threadably secured to a distal end of said rod; and
a prosthesis for a femoral head having a longitudinally extending stem having a bore extending along said stem, said bone being sized for slidably receiving said rod therein to guide and hold said stem in the bone cavity for cementing in place with a substantially uniform thickness of bone cement between said stem and the femur.

* * * * *

UNITED STATES PATENT AND TRADEMARK OFFICE
CERTIFICATE OF CORRECTION

PATENT NO. : 4,919,673

DATED : April 24, 1990

INVENTOR(S) : AHNS-GEORG WILLERT, et al

It is certified that error appears in the above-identified patent and that said Letters Patent is hereby corrected as shown below:

Column 2, line 67 "bond" should be -bone-

Signed and Sealed this

Twentieth Day of August, 1991

Attest:

HARRY F. MANBECK, JR.

Attesting Officer

Commissioner of Patents and Trademarks